(12) United States Patent
Fuentes et al.

(10) Patent No.: US 12,308,096 B2
(45) Date of Patent: May 20, 2025

(54) COMPUTER DEVICE FOR DETECTING AN OPTIMAL CANDIDATE COMPOUND AND METHODS THEREOF

(71) Applicant: Molecular Devices, LLC, San Jose, CA (US)

(72) Inventors: Emmanuel Israel Fuentes, Waukesha, WI (US); Gopal Biligeri Avinash, San Ramon, CA (US); Robert John Graves, San Ramon, CA (US); Abhijit Vijay Thatte, San Ramon, CA (US); Afek Kodesh, San Ramon, CA (US); Jeffery Caron, San Ramon, CA (US); Sharmistha Das, San Ramon, CA (US)

(73) Assignee: Molecular Devices, LLC, San Jose, CA (US)

( * ) Notice: Subject to any disclaimer, the term of this patent is extended or adjusted under 35 U.S.C. 154(b) by 0 days.

(21) Appl. No.: 18/119,992

(22) Filed: Mar. 10, 2023

(65) Prior Publication Data
US 2024/0013867 A1   Jan. 11, 2024

Related U.S. Application Data

(63) Continuation of application No. 16/336,549, filed as application No. PCT/EP2017/075003 on Oct. 2, 2017, now Pat. No. 11,636,924.
(Continued)

(51) Int. Cl.
*G16C 20/50* (2019.01)
*G06F 18/2321* (2023.01)
(Continued)

(52) U.S. Cl.
CPC ......... *G16C 20/50* (2019.02); *G06F 18/2321* (2023.01); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 6,615,141 B1 | 9/2003 | Sabry | |
| 7,246,012 B2 * | 7/2007 | Kutsyy | ............ G06F 18/24143 |
| | | | 382/128 |

(Continued)

FOREIGN PATENT DOCUMENTS

| | | |
|---|---|---|
| CN | 102165489 | 8/2011 |
| CN | 103827889 | 5/2014 |

(Continued)

OTHER PUBLICATIONS

Feng et al. ("Multi-Parameter Phenotypic Profiling: Using Cellular Effects to Characterize Small-Molecule compounds," Drug Discovery, 2009, 8:567-578 (Year: 2009).*

(Continued)

*Primary Examiner* — Anand P Bhatnagar
(74) *Attorney, Agent, or Firm* — Merchant & Gould P.C.

(57) ABSTRACT

The invention relates to a method for a computer device, for detecting an optimal candidate compound based on a plurality of samples comprising a cell line and one or more biomarkers, and a plate map configuration, wherein the plate map configuration is providing locations of samples comprising cell lines exposed to one or more biomarkers and different concentrations of a candidate compound forming at least one concentration gradient, the candidate compound being comprised in a plurality of can-didate compounds, said method comprising generating (310) phenotypic profiles of each concentration gradient of each of the plurality of candidate compounds at a plurality of successive points in time to form a plurality of compound profiles, wherein generating phenotypic profiles comprises the steps obtaining (312) image data depicting each sample comprised in the
(Continued)

concentration gradient, generating (314) a class-label and a class for each cell of the samples based on the image data, detecting (320) the optimal candidate compound by evaluating a comparison criterion on the plurality of compound profiles. Furthermore, the invention also relates to corresponding computer device, a computer program, and a computer program product.

20 Claims, 10 Drawing Sheets

Related U.S. Application Data

(60) Provisional application No. 62/402,272, filed on Sep. 30, 2016.

(51) Int. Cl.
| | | |
|---|---|---|
| *G06T 7/00* | (2017.01) | |
| *G06V 10/762* | (2022.01) | |
| *G06V 20/69* | (2022.01) | |
| *G16B 20/00* | (2019.01) | |
| *G01N 33/50* | (2006.01) | |

(52) U.S. Cl.
CPC .......... *G06T 7/0014* (2013.01); *G06V 10/763* (2022.01); *G06V 20/698* (2022.01); *G16B 20/00* (2019.02); *G01N 33/5008* (2013.01); *G06F 2218/16* (2023.01); *G06T 2200/24* (2013.01); *G06T 2207/30024* (2013.01)

(56) References Cited

U.S. PATENT DOCUMENTS

| | | | | |
|---|---|---|---|---|
| 8,664,363 | B2* | 3/2014 | Jones | C07K 16/2851 |
| | | | | 424/134.1 |
| 9,796,505 | B1* | 10/2017 | Venero | B65D 19/38 |
| 10,360,499 | B2* | 7/2019 | Kumar | G16B 40/20 |
| 11,636,924 | B2 | 4/2023 | Fuentes et al. | |
| 11,861,881 | B2 | 1/2024 | Ianni et al. | |
| 2004/0117124 | A1 | 6/2004 | Kiros et al. | |
| 2006/0045348 | A1* | 3/2006 | Kiros | G06F 18/40 |
| | | | | 382/190 |
| 2007/0208516 | A1 | 9/2007 | Kutsyy et al. | |
| 2008/0280771 | A1* | 11/2008 | Lubman | C40B 50/14 |
| | | | | 506/7 |
| 2009/0170091 | A1 | 7/2009 | Giuliano | |
| 2013/0101133 | A1 | 4/2013 | Yoon et al. | |
| 2013/0101199 | A1 | 4/2013 | Alexandrov et al. | |
| 2016/0272960 | A1 | 9/2016 | Thanos et al. | |
| 2017/0166878 | A9 | 6/2017 | Thanos et al. | |
| 2017/0272960 | A1* | 9/2017 | Li | H04L 41/5009 |
| 2018/0273621 | A1* | 9/2018 | Damschroder | A61P 19/02 |
| 2019/0111164 | A1* | 4/2019 | Rainey | A61K 51/1072 |
| 2021/0061906 | A1* | 3/2021 | Damschroder | A61P 5/40 |
| 2021/0147828 | A1* | 5/2021 | Ben-David | C12N 9/22 |
| 2023/0360208 | A1 | 11/2023 | Ianni et al. | |
| 2024/0013867 | A1 | 1/2024 | Fuentes et al. | |

FOREIGN PATENT DOCUMENTS

| | | |
|---|---|---|
| CN | 104204807 | 12/2014 |
| CN | 102687007 B | 7/2015 |
| CN | 104975063 | 10/2015 |
| CN | 111656393 A | 9/2020 |
| CN | 113454733 A | 9/2021 |
| GB | 2434225 | 7/2007 |
| JP | 2009-063508 | 3/2009 |
| JP | 2009-526519 | 7/2009 |
| JP | 2014-134524 | 7/2014 |
| JP | 6445127 B2 | 12/2018 |
| JP | 2022532615 A | 7/2022 |
| WO | 2012/096992 | 7/2012 |
| WO | 2022066725 A1 | 3/2022 |
| WO | 2023283321 A1 | 1/2023 |

OTHER PUBLICATIONS

Abraham et al., "Application of a High-Content Multiparameter Cytotoxicity Assay to Prioritize Compounds Based on Toxicity Potential in Humans," Society for Biomolecular Sciences, 2008, 527-537.
Bodenmiller et al., "Multiplexed Mass Cytometry Profiling of Cellular States Perturbed by Small-Molecule Regulators," Nature Biotechnology, 2012, 30(9):858-869.
Carpenter et al., "CellProfiler: Image Analysis Software for Identifying and Quantifying Cell Phenotypes," Genome Biology, 2006, 7(10) (11 pages).
Chan et al., "Cellometer Vision as an Alternative to Flow Cytometry for Cell Cycle Analysis, Mitochondrial Potential, and Immunophenotyping," Cytometry Part A, 2011, 79A:507-517.
Drawnel et al., "Disease Modeling and Phenotypic Drug Screening for Diabetic Cardiomyopathy Using Human Induced Pluripotent Stem Cells," Cell Reports, 2014, 9:810-820.
European Communication in Application 17787343.7, mailed Nov. 11, 2022, 7 pages.
Feng et al., "Multi-Parameter Phenotypic Profiling: Using Cellular Effects to Characterize Small-Molecule Compounds," Drug Discovery, 2009, 8:567-578.
Kawatani, Makoto et al., kemikarubaioroji to shinkibunshihyotekiyaku (chemical biology and novel molecule targeting drugs), Nippon Rinsho, Japan, Aug. 1, 2015, vol. 73, No. 8, Aug. 2015, pp. 1273-1280 (English abstract).
Ljosa et al., "Comparison of Methods for Image-Based Profiling of Celolular Morphological Responses to Small-Molecule Treatment," Journal of Biological Screening, 2013, 18(10): 1321-1329.
PCT International Preliminary Report on Patentability in Application PCT/EP2017/075003, mailed Apr. 11, 2019, 8 pgs.
PCT International Search Report and Written Opinion in Application PCT/EP2017/075003, mailed May 17, 2018, 11 pgs.
Price, Jeffrey et al., "High Throughput Microscopy: From Images to Data", in 3rd IEEE International Symposium Biomedical Imaging: Nano to Macro, https://ieeexplore.ieee.org/document/1624899, US IEEE, May 8, 2006, pp. 247-250.
European Communication in Application 17787343.7, mailed Apr. 2, 2025, 6 pages.
Han, Yuanyuan et al., "Review: Imaging technologies for flow cytometry", Lab on a Chip, vol. 16, No. 24, Jan. 1, 2016, pp. 4639-4647.

* cited by examiner

COMPUTER DEVICE FOR DETECTING AN OPTIMAL CANDIDATE COMPOUND AND METHODS THEREOF

CROSS-REFERENCE TO RELATED APPLICATIONS

This application is a continuation of U.S. patent application No. 16/336,549, filed Mar. 26, 2019, which is a National Stage Application of PCT/EP2017/075003, filed Oct. 2, 2017, which claims priority benefit of U.S. Provisional Application No. 62/402,272, filed on Sep. 30, 2016, the entire disclosures of which are hereby incorporated herein by reference.

TECHNICAL FIELD

The invention relates to a computer device for detecting an optimal candidate compound. Furthermore, the invention also relates to a corresponding method, a computer program, and a computer program product.

BACKGROUND

Testing and evaluating new compounds in experiments, e.g. compounds intended for medical use, may typically involve studying cellular mechanisms in a biological context to detect and/or select a candidate compound from a plurality of candidate compounds. Experiments comprising a plurality of samples, e.g. arranged according to a plate map configuration on determined locations a well-plate, may be conducted purely to discover or describe new insights into a biological phenotype. E.g. the observable characteristics or traits of cells under study. To interpret large, high dimensional (dense) cytometric data sets obtained from the experiments poses a problem for researchers and scientists, e.g. by generating statistical experiment insights and performing cell population classification. In particular, a disadvantage of conventional tools or systems for automatic classification of biological objects, such as cells in a sample, is that they require the user to leverage univariate and bivariate visualizations to determine cutoff regions and/or decision regions between classes and/or cell population regions. Further, determining decision regions between cell populations is rarely a linear clear-cut, population granularity may be difficult to understand, when analyzing cytometric data sets of an experiment visually by using a single measure and potentially performing iterative analysis of a single field-of-view (FOV). Further manual cytometric cellular measure investigations are labor intensive and it is difficult to select which cytometric cellular measure measures to us in the analysis and which contain the best ability to split a population and is therefore vulnerable to human error. Some conventional systems apply a two phase manual process involving visual cellular labeling and supervised cellular classification. The use of these systems involves the user to bin cellar objects as exemplars of a respective cell population manually by clicking cells and annotating them via manual text entry. A disadvantage of this is that it is a relatively slow and labor intensive process. As it is usually performed by viewing image data depicting single field of view, which rarely represents the entire cell population when a dose response is present, it has the disadvantage of reducing predictive modeling possibilities and thus limiting the potential inherent in the large and dense data sets available. A trend in conventional systems is to try and circumvent features extraction and/or cytometric features, as they are bound by human understanding, and instead rely on machine learning features, e.g. measures and/or features that may be extracted by a computer with less effort than cytometric features. Disadvantage of using machine learning features is that they are hard or impossible to understand or interpret by a user and that they therefore do not allow the user to evaluate and exclude the viability and/or deviation of input and/or intermediate data.

Thus there is a need to provide a solution which mitigates or solves the drawbacks and problems of conventional solutions.

SUMMARY

An objective of embodiments of the invention is to provide a solution which mitigates or solves the drawbacks and problems of conventional solutions. The above and further objectives are achieved by the subject matter of the independent claims. Further advantageous implementation forms of the invention are defined by the dependent claims.

According to a first aspect of the invention, the above mentioned and other objectives are achieved with a computer device for detecting an optimal candidate compound based on a plurality of samples comprising a cell line and one or more biomarkers. Detecting the optimal candidate compound is further based on a plate map configuration. The plate map configuration is providing locations of samples comprising cell lines exposed to one or more biomarkers and different concentrations of one or more candidate compounds forming at least one concentration gradient, the candidate compound being comprised in a plurality of candidate compounds, the computer device comprising a processor, and a memory, said memory containing instructions executable by said processor, whereby said computer device is operative to generate phenotypic profiles of each concentration gradient of each of the plurality of candidate compounds at a plurality of successive points in time to form a plurality of compound profiles. The computer device is further operative to generate phenotypic profiles further by further obtain image data depicting each sample comprised in the concentration gradient, and to generate a class-label and a class for each cell of the samples based on the image data. The computer device is further operative to detect the optimal candidate compound by evaluating a comparison criterion on the plurality of compound profiles.

An advantage of this aspect is that statistical experiment insights, e.g. to detect optimal candidate compounds, is improved by processing large, high dimensional (dense) cytometric data sets relating to a plate map configuration in an efficient manner by generating compound profiles and detecting an optimal candidate compound by evaluating a comparison criterion on the plurality of compound profiles. A further advantage is that the required time and labor can be reduced by generating class-labels and classes and/or cell population regions with minimal to no human interaction.

In a first possible implementation form of the computer device according to the first aspect, the computer device further comprising an input device and a display, wherein the computer device is further operative to select an exemplary subset of image data depicting at least one cell of the samples for each class-label and/or class, display the exemplary subset of image data and the respective class-label and/or class on the display to a user, receive user input data from the input device, indicated by a user, indicative of a operation on at least one class-label and/or class and perform the operation on the class-label and/or class of cells of the samples based on the user input data. In an embodiment of the first implementation form, the computer device is further operative to perform the operation selected from one of add class, delete class, split class or merge class.

An advantage of this implementation form is to provide visualization familiarity and conceptual understanding to a user and allows for iterative user corrections, thus improving classification quality and/or reliability.

In a second possible implementation form of the computer device according to the first implementation form of the first aspect or the first aspect as such, the computer device is operative to detect the optimal candidate compound by further obtain one or more reference compound profiles, calculate a multi-dimensional differential value for each compound profile of the plurality of compound profiles based on the one or more reference compound profiles, detect the optimal candidate compound by evaluating a comparison criterion on the plurality of compound profiles, wherein the comparison criterion is evaluated based on the multi-dimensional differential values. In an embodiment of this implementation form, the multi-dimensional differential value is preferably N dimensional, with N greater than or equal to 2. More preferably, the multi-dimensional differential value is N dimensional, with N greater than 3.

An advantage of this implementation form is that the quality of the detection of a candidate compound is improved by improving the reliability and/or quality by evaluating over high dimensional (dense) data sets comprising compound profiles.

In a third possible implementation form of the computer device according to the first or second implementation form of the first aspect or the first aspect as such, the computer device is operative to obtain the image data depicting each sample comprised in the concentration gradient from a plurality of field of views and/or the image data is depicting each sample comprised in the concentration gradient processed with a plurality of image filters.

An advantage of this implementation form is that the quality of the phenotypic profiles and thus the compound profiles is improved by improving the reliability and/or quality when generating class-labels and a class for cell of the samples, as the cells are depicted using a plurality of field of views and/or depicted using a plurality of image filters.

In a fourth possible implementation form of the computer device according to any preceding implementation form of the first aspect or the first aspect as such, the computer device is operative to generate phenotypic profiles by further generate a cytometric parameter set for each cell based on the image data to form a first collection of cytometric parameter sets and generate a phenotypic classification model, configured to map a cytometric parameter set to a class and/or phenotypic class, based on a parameter similarity function and the first collection, wherein the parameter similarity function is configured to correlate cytometric parameter sets of the first collection to each other. In an embodiment of the fourth implementation form, the computer device is operative generate phenotypic profiles by further generate a phenotypic classification model, configured to map a cytometric parameter set to a class, based on a parameter similarity function and the first collection, wherein the parameter similarity function is configured to correlate cytometric parameter sets of the first collection to each other.

An advantage of this implementation form is that the vulnerability to human error is reduced as a, e.g. a high dimensional or dense, cytometric parameter set is used for classification contrary to conventional methods relying on a single cytometric parameter and/or cytometric cellular measure chosen by the user. A further advantage of this implementation form is that the generated classes of the phenotypic classification model can be reused on a successive experiments, thus further improving predictive modeling possibilities and further reducing the required time and labor.

In a fifth possible implementation form of the computer device according to any preceding implementation form of the first aspect or the first aspect as such, the computer device is further operative to display the phenotypic profiles and/or compound profiles on the display.

An advantage of this implementation form is that the users understanding is improved and thus the time required for detection is reduced by visualizing the intermediate and end results to the user.

In a sixth possible implementation form of the computer device according to any of the preceding implementation forms of the first aspect or the first aspect as such, the concentration gradients of a candidate compound comprises a plurality of separate wells, wherein each well comprises a sample of the cell line exposed the one or more biomarkers and different concentrations of the candidate and is arranged according to the plate map configuration on one or more well-plates.

According to a second aspect of the invention, the above mentioned and other objectives are achieved with a method for a computer device, for detecting an optimal candidate compound based on a plurality of samples. The samples may comprise a cell line and one or more biomarkers. Detecting the optimal candidate compound is further based on a plate map configuration. The plate map configuration is providing locations of samples comprising cell lines exposed to one or more biomarkers and different concentrations of one or more candidate compounds forming at least one concentration gradient. The candidate compound/s is comprised in a plurality of candidate compounds. The method comprising generating phenotypic profiles of each concentration gradient of each of the plurality of candidate compounds at a plurality of successive points in time to form a plurality of compound profiles, wherein generating phenotypic profiles comprises the steps obtaining image data depicting each sample comprised in the concentration gradient, generating a class-label and a class for each cell of the sample based on the image data, detecting the optimal candidate compound by evaluating a comparison criterion on the plurality of compound profiles.

An advantage of this aspect is that statistical experiment insights, e.g. to detect optimal candidate compound, is improved by processing large, high dimensional (dense) cytometric data sets relating to a plate map configuration in an efficient manner by generating compound profiles and detecting an optimal candidate compound by evaluating a comparison criterion on the plurality of compound profiles. A further advantage is that the required time and labor can be reduced by generating class-labels and classes and/or cell population regions without human interaction.

In a first possible implementation form of the method according to the second aspect, further comprising the steps selecting an exemplary subset of image data depicting at least one cell of the samples for each class-label and/or class, displaying the exemplary subset of image data and the respective class-label and/or class to a user, receiving user input data from the user indicative of an operation on at least one class, performing the operation on the class-label and/or class of the least one cell of the samples based on the user input data. In an embodiment of the first implementation form, the operation on at least one class is selected from add class, delete class, split class or merge class.

An advantage of this implementation form is to provide visualization familiarity and conceptual understanding to a user and allows for iterative user corrections, thus improving classification quality and/or reliability.

In a second possible implementation form of the method according to the first implementation form of the second aspect or the second aspect as such, the method step of detecting the optimal candidate compound further comprises obtaining one or more reference compound profiles, calculating a multi-dimensional differential value for each compound profile of the plurality of compound profiles based on the one or more reference compound profiles, detecting the optimal candidate compound by evaluating a comparison criterion on the plurality of compound profiles, wherein the comparison criterion is evaluated based on the multi-dimensional differential values.

In a third possible implementation form of the method according to the first or second implementation form of the second aspect or the second aspect as such, the image data is depicting each sample comprised in the concentration gradient from a plurality of field of views and/or the image data is depicting each sample comprised in the concentration gradient processed with a plurality of image filters.

An advantage of this implementation form is that the quality of the phenotypic profiles and thus the compound profiles is improved by improving the reliability and/or quality when generating class-labels and a class for cell of the samples, as the cells are depicted using a plurality of field of views and/or depicted using a plurality of image filters.

In a fourth possible implementation form of the method according to any preceding implementation form of the second aspect or the second aspect as such, generating phenotypic profiles further comprises generating a cytometric parameter set for each cell based on the image data to form a first collection of cytometric parameter sets and generating a phenotypic classification model, configured to map a cytometric parameter set to a class and/or phenotypic class, based on a parameter similarity function and the first collection, wherein the parameter similarity function is configured to correlate cytometric parameter sets of the first collection to each other. In an embodiment of the fourth implementation form, generating phenotypic profiles further comprises generating a phenotypic classification model, configured to map a cytometric parameter set to a class, based on a parameter similarity function and the first collection, wherein the parameter similarity function is configured to correlate cytometric parameter sets of the first collection to each other.

An advantage is that the vulnerability to human error as classification is reduced as a cytometric parameter set is used for classification contrary to conventional methods relying on a single cytometric parameter and/or cytometric cellular measure chosen by the user. A further advantage of this implementation form is that the generated classes of the phenotypic classification model can be reused on a successive experiment, thus further improving predictive modeling possibilities and further reducing the required time and labor.

According to a third aspect of the invention, the above mentioned and other objectives are achieved with a computer program comprising computer-executable instructions for causing a computer device, when the computer-executable instructions are executed on a processing unit comprised in the computer device, to perform the method steps of generating phenotypic profiles of each concentration gradient of each of a plurality of candidate compounds at a plurality of successive points in time to form a plurality of compound profiles, wherein generating phenotypic profiles comprises the steps obtaining image data depicting each sample comprised in the concentration gradient, generating a class-label and a class for each cell of the samples based on the image data, detecting the optimal candidate compound by evaluating a comparison criterion on the plurality of compound profiles.

In a first possible implementation form of the computer program according to the third aspect, further causing the computer device to perform the method steps of select an exemplary subset of image data depicting at least one cell of the samples for each class-label and/or class, display the exemplary subset of image data and the respective class-label and/or class to a user, receive user input data from the user indicative of an operation on at least one class-label and/or class, and perform the operation on the class-label and/or class of cells of the samples based on the user input data.

In a second possible implementation form of the computer program according to the first implementation form of the third aspect or the third aspect as such, further causing the computer device to perform the method step of detecting the optimal candidate compound by further performing the method steps of obtaining one or more reference compound profiles, calculating a multi-dimensional differential value for each compound profile of the plurality of compound profiles based on the one or more reference compound profiles, detecting the optimal candidate compound by evaluating a comparison criterion on the plurality of compound profiles, wherein the comparison criterion is evaluated based on the multi-dimensional differential values.

According to a fourth aspect of the invention, the above mentioned and other objectives are achieved with a computer program product comprising a computer-readable storage medium, the computer-readable storage medium having the computer program according to any of the possible implementation forms of the computer program according to the first implementation form of the third aspect or the third aspect as such.

The advantages of the second to fourth aspects are the same as the corresponding method according to the first aspect.

Further applications and advantages of embodiments of the invention will be apparent from the following detailed description. The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

The appended drawings are intended to clarify and explain different embodiments of the invention, in which.

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
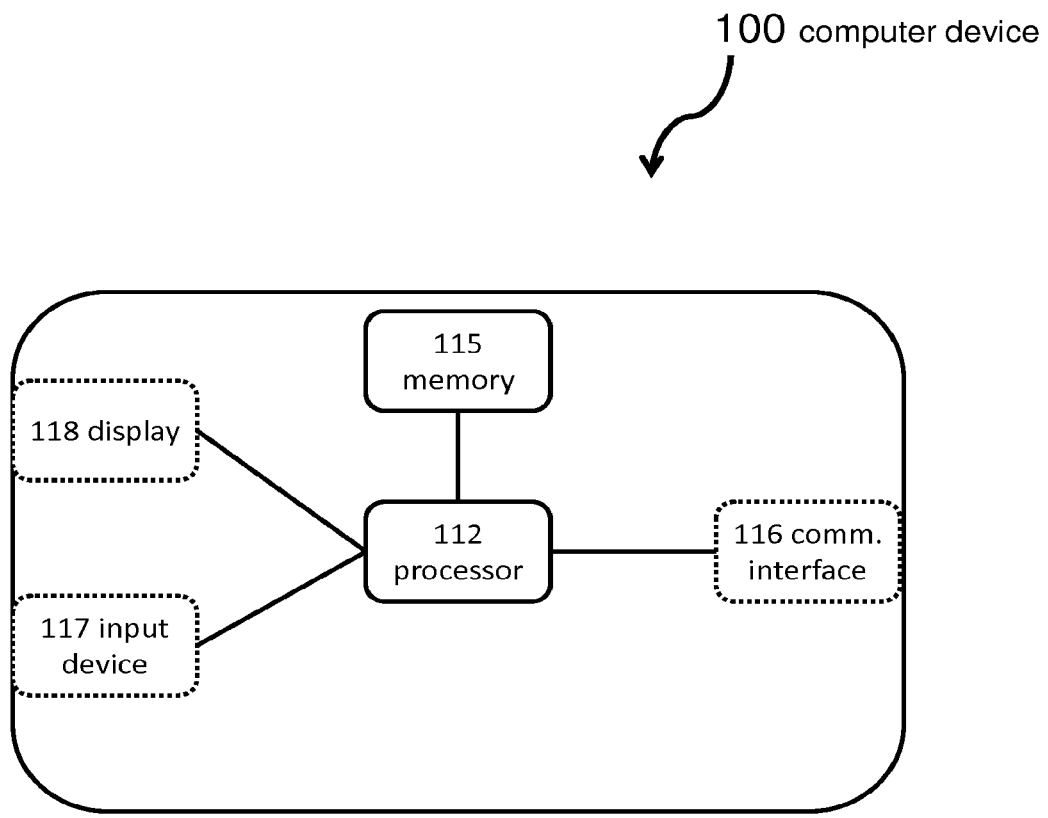
FIG. 1 shows a diagram of a computer device according to an embodiment of the invention.

FIG. 1 shows a diagram of a computer device 100 according to an embodiment of the invention. In yet an embodiment, the computer device 100 is in the form of a cell experiment evaluation device, a server, a stationary computing device, a laptop computer, a tablet computer, a handheld computer, a wrist-worn computer, a smart watch, a PDA, a smartphone, a smart TV, a telephone, a media player, a game console, a vehicle mounted computer system or a navigation device. In embodiments, the computer device 100 comprises a processor and/or processing means 112 comprising and/or in the form of a processor/processing unit, e.g. processing circuitry, a central processing unit, processor modules or multiple processors configured to cooperate with each-other. The processor and/or processing means may be provided, e.g. in a memory, with specifically designed programming or program code portions adapted to control the processing means 112 to perform the steps and functions of one or more embodiments of the method and/or methods described herein. The computer device 100 may further comprise at least one memory 115 or data storage configured to store the programming or program code portions and/or data values or parameters received as a write signal from the processing means 112. The at least one memory 115 or data storage may further be configured to retrieve and send data values and/or parameters as a read signal to the processing means 112. The computer device 100 may further comprise a communications interface 116, e.g. a wireless transceiver and/or communications network adapter, which is configured to send and/or receive data values or parameters as a signal to or from the processing means 112 to or from other external nodes, such as a database or an image generator. In an embodiment, the communications interface 116 communicates directly between nodes or via a communications network. In one or more embodiments the computer device 100 may further comprise an input device 117, configured to receive input or indications from a user and send a user-input signal indicative of the user input or indications to the processing means 112. In one or more embodiments the computer device further comprises a display 118 configured to receive a display signal indicative of rendered objects, such as text or graphical user input objects, from the processing means 112 and to display the received signal as objects, such as text or graphical user input objects. In one embodiment the display 118 is integrated with the user input device 117 and is configured to receive a display signal indicative of rendered objects, such as text or graphical user input objects, from the processing means 112 and to display the received signal as objects, such as text or graphical user input objects, and/or configured to receive input or indications from a user and send a user-input signal indicative of the user input or indications to the processing means 112. In an example, the input data is indicated by a user and is indicative of an operation on at least one class-label and/or class. In embodiments, the processing means 112 is communicatively coupled to the memory 115 and/or the communications interface and/or the input device and/or the display and/or optional sensor/s (not shown in the figure). In embodiments, the communications interface 116 communicates using wired and/or wireless communication techniques. In embodiments, the one or more memories 115 may comprise a selection of a hard RAM, disk drive, a floppy disk drive, a magnetic tape drive, an optical disk drive, a CD or DVD drive (R or RW), or other removable or fixed media drive.

In an embodiment, a computer device 100 is provided for detecting an optimal candidate compound, e.g. in an experiment. In an example, the experiment is configured to measure within the cells one or more biomarkers labelled with fluorescent tags, which are imaged by the computer device, and which are predicted to provide insight into the biological process(es) under investigation. Detecting the optimal candidate compound may be based on a plurality of samples comprising a cell line and one or more biomarkers. In an example, the plurality of samples may comprise a cell line of mammalian origin. In yet another example, the cell line is derived from other species or may comprise cells extracted from tissue such as Human Tissue, or any other content which is suitable to go into a microtitter plate for the described purpose.

The one or more biomarkers may be fluorescent proteins produced by genetically modified cell lines, such as Green fluorescent protein (GFP) from the jellyfish *Aequorea victoria*, or fluorescently labeled antibodies used to detect native proteins. In a further example, fluorescent cell stains such "4',6-diamidino-2-phenylindole" (DAPI) is used for nucleus or nucleic acid and a variety of other cell-permeant fluorescent stains can be used to label other cellular structures.

Detecting the optimal candidate compound may further be based on a plate map configuration 230. The plate map configuration 230 is providing locations of samples, e.g. arranged on a well-plate, comprising cell lines exposed to the one or more biomarkers and different concentrations of one or more candidate compounds forming at least one concentration gradient 660. In an example, the plate map configuration is in the form of a data structure indicating e.g. a well-plate identity and pairs of rows and columns, stored in memory 115 and/or an external node and/or an internal or external database. In a further example, the plate map configuration is providing locations of samples comprising cell lines fluorescently labeled for one or more biomarkers and/or, exposed to one or more biomarkers and different concentrations of one or more candidate treatments/compounds, which may comprise various compounds of natural or synthetic origin, with predicted or unknown effects, and compounds which may be arrayed in the form forming the at least one concentration gradient. The plate map configuration may further indicate the location on the well-plate of a candidate compound and the concentration of the candidate compound, e.g. a solute in a solvent. In a further example, the plate map configuration is indicating the locations of samples over a plurality of well-plates. The samples of the one or more candidate compounds may be arranged and/or have a location on the well-plate/s according to the plate map configuration 230. The candidate compound may be comprised in a plurality of candidate compounds, e.g. multiple candidate compounds tested for a particular purpose or effect. The computer device 100 may further comprise a processor 115, and a memory 115. As further described above, said memory 115 containing instructions executable by said processor 112. Said processor 112 may be a processing circuitry, a central processing unit, processor modules or multiple processors configured to cooperate with each-other. The computer device 100 may be operative to generate phenotypic profiles of each concentration gradient 660, e.g. of each candidate compound, of the plurality of candidate compounds at a plurality of successive points in time to form a plurality of compound profiles. In an example, phenotypic profiles of a concentration gradient may comprise a cell count of each class and/or a phenotypic class for each sample comprised in the concentration gradient, where each sample comprises different concentrations of the candidate compound. Phenotypic profiles are further described in relation to FIG. 9. The computer device 100 may be further be operative to generate phenotypic profiles by further performing the steps obtain image data depicting each sample comprised in the concentration gradient, generate a class-label and a class for each cell of the samples and/or each sample comprised in the concentration gradient based on the image data, detect the optimal candidate compound by evaluating a comparison criterion on the plurality of compound profiles. The comparison criterion and/or criteria may be a loss function and/or or cost function and/or minimization criterion available to the person skilled in the art. In an example, a phenotypic profile comprises data indicative of a cell count, as an absolute number or a percentage % of the total number of cell in a sample, for each class in a sample of a concentration gradient 660 of a candidate compound. In yet an example, a concentration profile comprises data indicative of a cell count for a class and a concentration of a concentration gradient 660 of a candidate compound. In yet an example, a phenotypic profile may comprise a plurality of concentration profiles. In an example, obtaining image data depicting each sample comprised in the concentration gradient comprises retrieving and/or receiving the image data from the memory 115, retrieving and/or receiving the image data from an external node, retrieving and/or receiving the image data from an internal and/or external database or retrieving and/or receiving the image data from an image generator. In an example, generate a class-label and a class comprises segmenting image data for each cell as a cell object and/or generating a cytometric parameter set for each cell as the cell object based on the image data. The cell object may be implemented as a data structure.

In a use case embodiment, the disclosure may be used in baseline phenotyping of cells where possible changes in the known cellular phenotype due to experimental perturbation of the cells is investigated. The experiment may be conducted purely to discover or describe new insights into a biological phenotype, i.e. the observable characteristics or traits of the cells under study. The types of experimental perturbation can include observing the effects of inhibiting or promoting enzyme activities in cells, often using genetic modification techniques, large-scale drug screening campaigns to discover bio-active molecules, and cell-based toxicology testing. A defining characteristic of these studies is the presence of a known phenotype and the goal is to compare phenotypic profiles in treated samples of cells in a cell line versus non-treated control samples of the same cell line. Since these experiments are commonly conducted in multi-well-plates, there is a requirement to map the physical experimental layout to the observed results, e.g. as a plate map configuration. In this example, the phenotypic profiling of the samples may require classification of a single cell type into different sub-classes, such as cell-cycle status. There is also an increasing trend to develop cellular models for tissues, where mixed cell types may be present, requiring cell-type specific classification tools. The present disclosure provides a semi-supervised pipeline which aims to simplify the workflow of user objectives, such as having quicker and more accurate classification. The present disclosure leverages a computer device and a method thereof, which is well suited to generate class-labels and/or classes based on such data properties. In a further example generating a class-label and a class for each cell of the samples based on the image data may be performed by using unsupervised clustering and/or classification algorithms such as k-means to derive intrinsic classes within the entire N-dimensional cell-by-cell data and/or cytometric parameter set. In a further example any clustering and/or classification algorithm from the family of unsupervised clustering techniques could be used, e.g. Ward Clustering, Hierarchical Clustering or Self Organizing Maps.

In the present disclosure, the generation of a class-label and a class for each cell of the samples may also involve the generation of a phenotypic classification model, e.g. an expression-based model. The present disclosure may also allow for iterative user corrections and deliver an expression based model with minimal to no user interaction by default. The present disclosure has multiple advantages such as quicker time from candidate compound to product, more accurate data manipulation, elimination of user error, elimination of requirement of prior user knowledge, continuous growth and learning as part of machine learning, ability to create phenotypic profile library/repository, provide an ability to extrapolate knowledge/resources to create affordable solutions for customers and provides higher fidelity workflow. As a further example of the complexity of the problem to classify cells based on high-dimensional cytometric data. Image derived cytometric data is naturally high dimensional and large in volume, quantity and/or storage space. For each image data channel of the image data, e.g. wavelength band such as color, acquired there are an increasing number of image features, which can be extracted. A simple experiment with two image data channels will have around 30 measurements. The complexity of the problem is quickly in the realm of the "curse of dimensionality". A modest pilot study typically generates a data set on the order of a few terabytes. There are around 300 to 500 cellular objects and/or cell objects comprised in image data comprising a single field of view based on the magnification used during image acquisition and/or capturing and/or generation. With image data comprising about three fields of views depicting a sample in a well, 96 wells on the most common microtiter plate and/or plate map configuration and/or well-plate experiments, and several hundred plate map configurations and/or well-plates per screen, the number of total cellular objects can reach the millions. Thus the need to reduce required time and labor requirements for detecting a candidate compound is very high.

In an embodiment, a computer device 100 is provided further comprising an input device 117 and a display 118, wherein the computer device 100 is further operative to select an exemplary subset of image data depicting at least one cell of the samples for each class-label and/or class, display the exemplary subset of image data and the respective class-label and/or class on the display 118, to a user, receive user input data from the input device 117, indicated by a user, indicative of a operation on at least one class-label and/or class and perform the operation on the class-label and/or class of cells of the samples based on the user input data. In an embodiment of the first implementation form, the computer device 100 is further operative to perform the operation selected from one of add class, delete class, split class or merge class. In an example, cells of the same class, e.g. "dead", have been classified as a first and second group and/or class. The user looking at the exemplary subset of image data on the display realizes that they should in fact be in the same class, may determine that the first and second group and/or class should be merged and makes an indication of this via the input device. The computer device 100 may then set the class and/or class-label information of the second group/class to be identical to the first group/class, effectively merging cells and/or cell objects of the two classes into a single class. In yet an example, the subset of image data depicting at least one cell is displayed in the form of a 2D thumbnail and the respective class-label and/or class is displayed as a rectangle enclosing one or more thumbnails, further described in relation to FIG. 8.

In an embodiment, a computer device is provided that is further operative to display the phenotypic profiles and/or compound profiles on the display 118. In one example, the phenotypic profiles are displayed as a line graph and the compound profiles are displayed as a box plot. In a further example, the phenotypic profiles and/or compound profiles are displayed on the display as a line graph plot displaying cell count for each respective class over compound concentration and/or concentration gradient and over a plurality of successive points in time and/or over time. The phenotypic profiles and/or compound profiles may be displayed as a line plot, as a regression plot, or as a surface plot.

In an embodiment, a computer device is provided that is further operative, when detecting the optimal candidate compound, to obtain one or more reference compound profiles, calculate a multi-dimensional differential value for each compound profile of the plurality of compound profiles based on the one or more reference compound profiles, detect the optimal candidate compound by evaluating a comparison criterion on the plurality of compound profiles, wherein the comparison criterion is evaluated based on the multi-dimensional differential values. The comparison criterion and/or criteria may be a loss function and/or cost function and/or minimization criterion. In one example the comparison criterion is a three-dimensional Z-value and/or standard indicating a signed number of standard deviations by which an observation or datum differs from the mean. In a further example a reference compound profiles dictates a cell count of 90% "not dead", 3% "dead" and 7% "other. The compound profile indicates a respective cell count over different concentrations and over time. The multi-dimensional differential value may be calculated as a three-dimensional Z-value and/or as a geometric mean of the difference cell count of each class.

In an embodiment, a computer device is provided where concentration gradients of a candidate compound comprise a plurality of separate wells 620, wherein each well 620 comprises a sample of the cell line exposed the one or more biomarkers and different concentrations of the candidate and is arranged according to the plate map configuration 230 on a well-plate.

Figure 2:
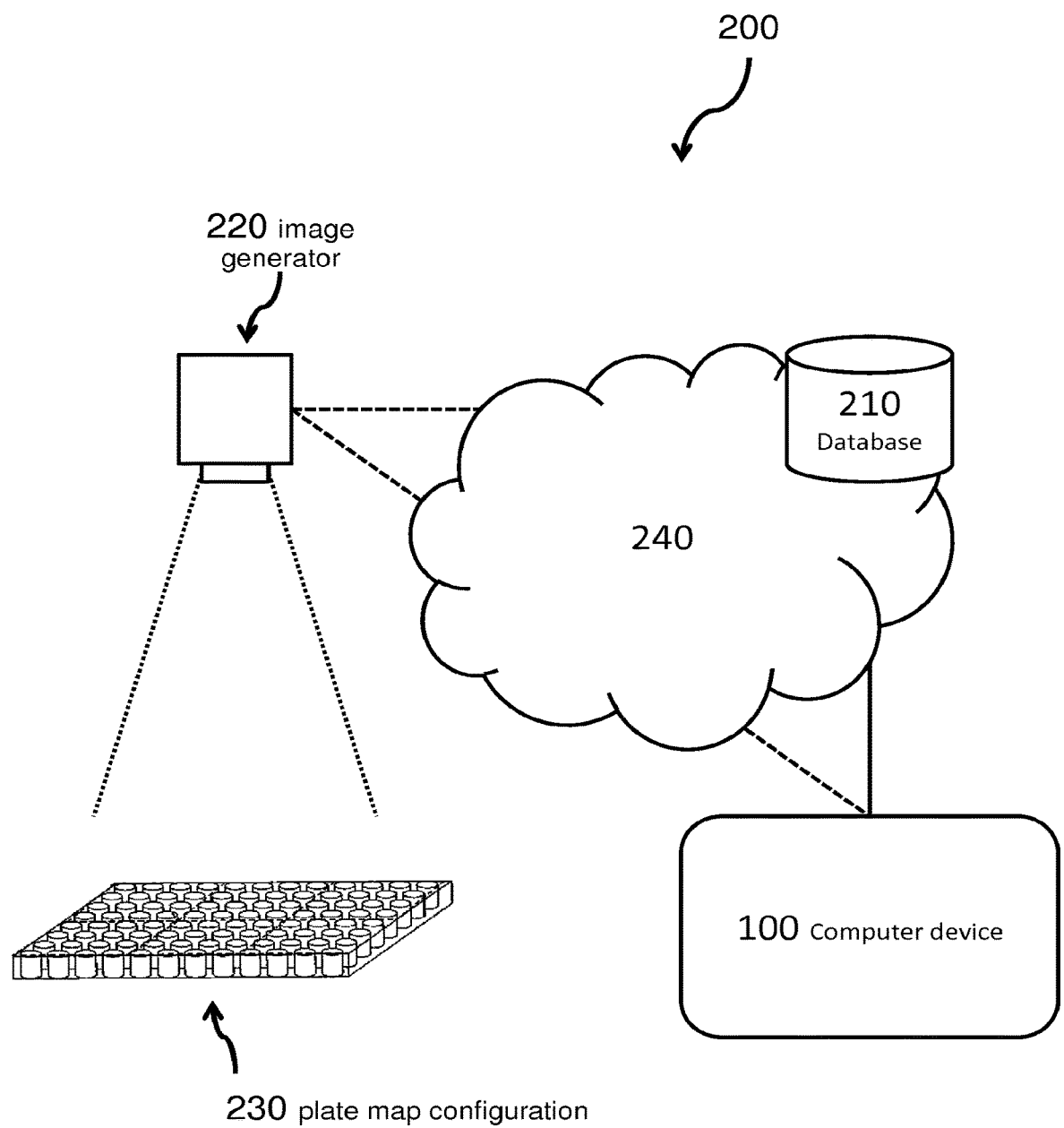
FIG. 2 shows a diagram of a candidate compound detection system comprising the computer device according to an embodiment of the invention.

FIG. 2 shows a diagram of a candidate compound detection system 200 comprising the computer device 100 according to an embodiment of the invention. The system 200 may comprise a computer device 100, as further described in relation to FIG. 1. The system may further comprise a database 210, e.g. a relational database, an object-relational database, XML database, NoSQL database or a NewSQL database. The database 210 may be configured to store data, such as image data, and send to the computer device 100 directly or via a communications network 240. The communications network may be any wired or wireless communications network. The communications network 240 may be selected from Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto. The system may further comprise an image generator 220. The image generator 220 may be configured to generate image data and send to the computer device 100 directly or via the communications network 240. The system may further comprise one or more plate map configurations 230 and/or respective well-plates. The image generator 220 may be configured to generate image data depicting the one or more samples arranged according to and/or on plate map configurations 230 and/or well-plates. The plate map configuration 230 and/or well-plate may represent and/or comprise a plurality of separate wells or receptacles configured to receive a sample. Each well may comprise a sample comprising a cell line exposed to one or more biomarkers and a determined concentration of a candidate compound of a concentration gradient and is arranged according to the plate map configuration, e.g. on a well-plate.

A plurality of wells comprised in the one or more plate map configurations 230 and/or well-plates may comprise samples of a cell line exposed to one or more biomarkers, which may be the same one or more biomarkers, and different concentrations of a candidate compound thereby forming at least one concentration gradient. In an example, cells of a cell-line are comprised in wells and/or samples arranged in a first column of the plate map configuration and/or well-plate are exposed to the same one or more biomarkers and a first concentration gradient and/or different concentrations of a first candidate compound. Further, cells of the samples comprised in each well arranged in a second column of the plate map configuration and/or well-plate is exposed to the same one or more biomarkers and a second concentration gradient and/or different concentrations of a second candidate compound. In a further example, different concentrations of a candidate compound are distributed over multiple columns. In a further example the plurality of candidate compounds is distributed over a plurality of plate map configurations and/or well-plates. The image generator 220 may be configured to generate and/or capture image data depicting each concentration gradient, e.g. depicting each sample comprised in each well comprising different concentrations of the candidate compound. In one example, the image generator 220 is selected from the group of visual light digital cameras, infrared digital cameras or radiology systems such as X-ray, radiography, ultrasound, computed tomography (CT), nuclear medicine including positron emission tomography (PET), and magnetic resonance imaging (MRI) systems. In a further example, the image generator 220 use fluorescent microscopy and/or traditional bright field technology. The image data may be represented as pixels, voxels or as vector data. The image data may comprise a plurality a plurality of field of views of each sample of cells of the sample comprised in each well and/or the image data may comprise multiple versions of a source image depicting each sample comprised in the concentration gradient processed with a plurality of image filters.

In a further aspect of the invention, methods according to the present disclosure are provided.

In an embodiment, a method is provided that comprises generating 310 phenotypic profiles of each concentration gradient 660 of each of a plurality of candidate compounds at a plurality of successive points in time to form a plurality of compound profiles, and, detecting 320 the optimal candidate compound by evaluating a comparison criterion on the plurality of compound profiles.

Figure 3:
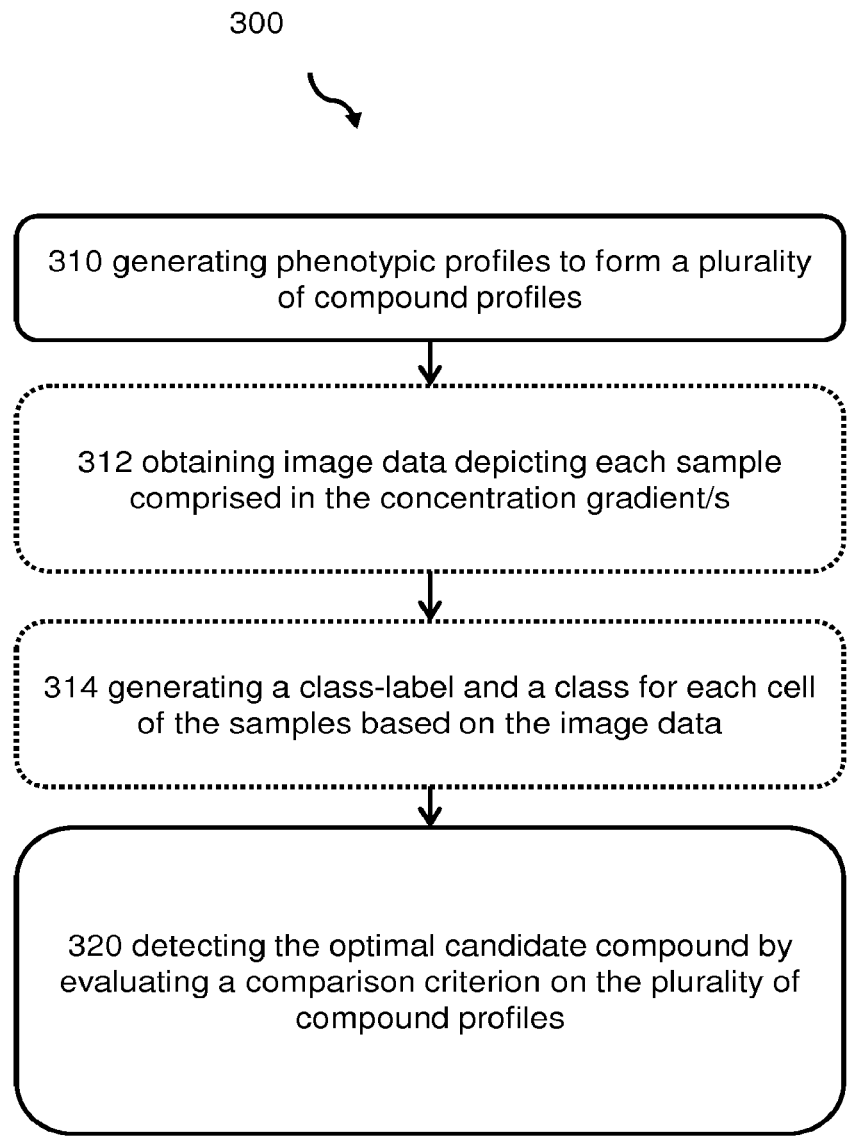
FIG. 3 shows a flowchart of a method for a computer device, for detecting an optimal candidate compound based on a plurality of samples according to an embodiment of the invention.

FIG. 3 shows a flowchart of a method for a computer device 100, for detecting an optimal candidate compound based on a plurality of samples according to an embodiment of the invention. The samples may comprise at least a cell line, one or more biomarkers. The samples may be arranged on and/or according to a plate map configuration 230 and/or on a well-plate. The plate map configuration 230 may be providing locations of samples comprising cell lines exposed to one or more biomarkers and different concentrations of one or more candidate compounds forming at least one concentration gradient 660, e.g. arranged according to the plate map configuration 230. The candidate compound may be comprised in a plurality of candidate compounds, e.g. multiple compounds part of an experiment. In an embodiment, the method comprises generating 310 phenotypic profiles of each concentration gradient 660 of each of the plurality of candidate compounds at a plurality of successive points in time to form a plurality of compound profiles, wherein generating phenotypic profiles comprises the steps obtaining 312 image data depicting each sample comprised in the concentration gradient, generating 314 a class-label and a class for each cell of the samples based on the image data and detecting 320 the optimal candidate compound by evaluating a comparison criterion on the plurality of compound profiles.

Figure 4:
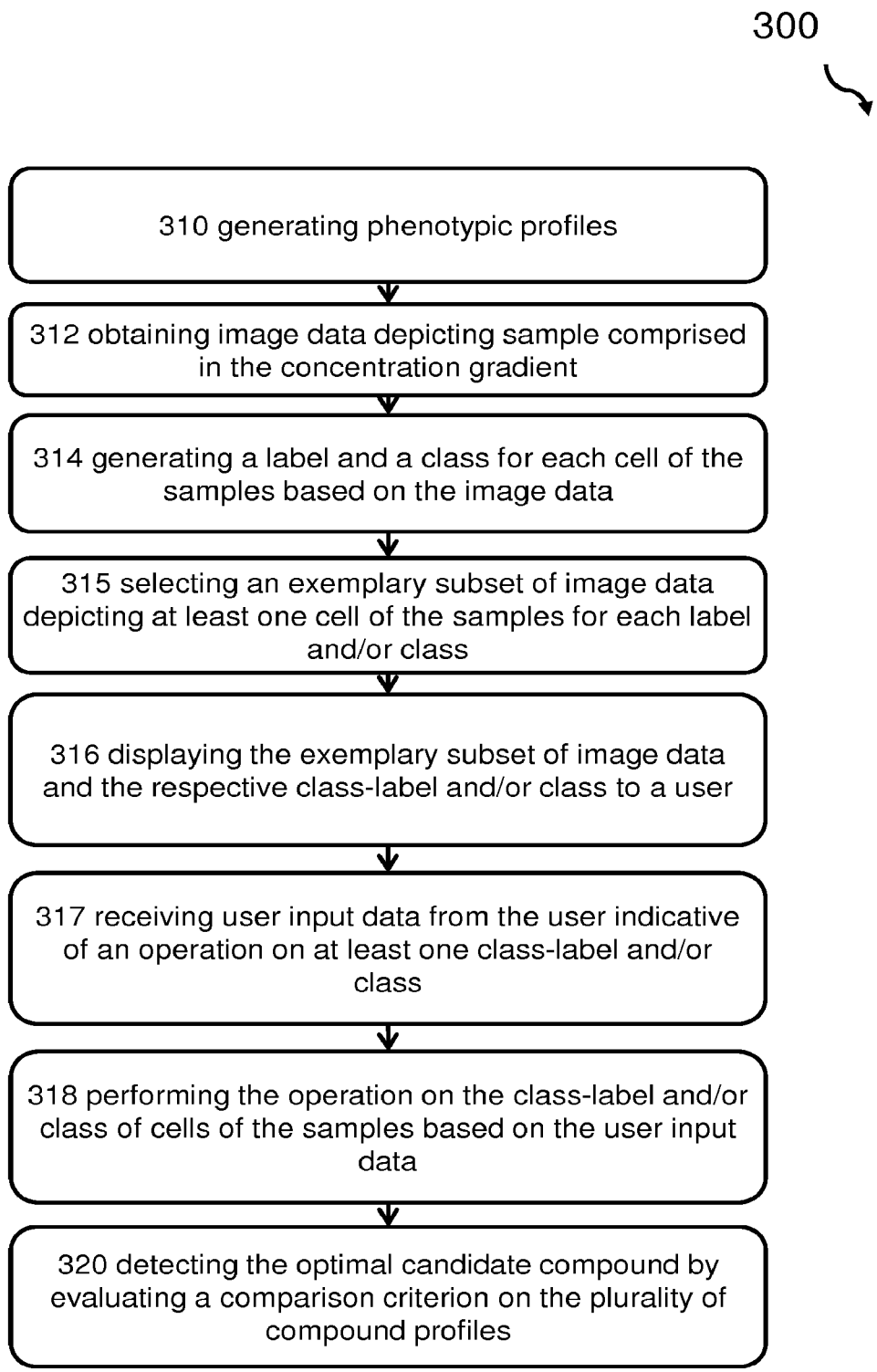
FIG. 4 shows a flowchart of a method according to yet an embodiment of the invention.

FIG. 4 shows a flowchart of a method according to yet an embodiment of the invention. The method further comprises the steps of selecting 315 an exemplary subset of image data depicting at least one cell of the samples for each class-label and/or class, displaying 316 the exemplary subset of image data and the respective class-label and/or class to a user, receiving 317 user input data from the user indicative of an operation on at least one class, performing 318 the operation on the class-label and/or class of cells of the samples based on the user input data. In an embodiment of the first implementation form, the operation on at least one class is selected from add class, delete class, split class or merge class. In an example, the exemplary subset of image data is selected by calculating a confidence measure of how well the image data represents the class and select the exemplary subset as the image data with the highest confidence measure.

Figure 5:
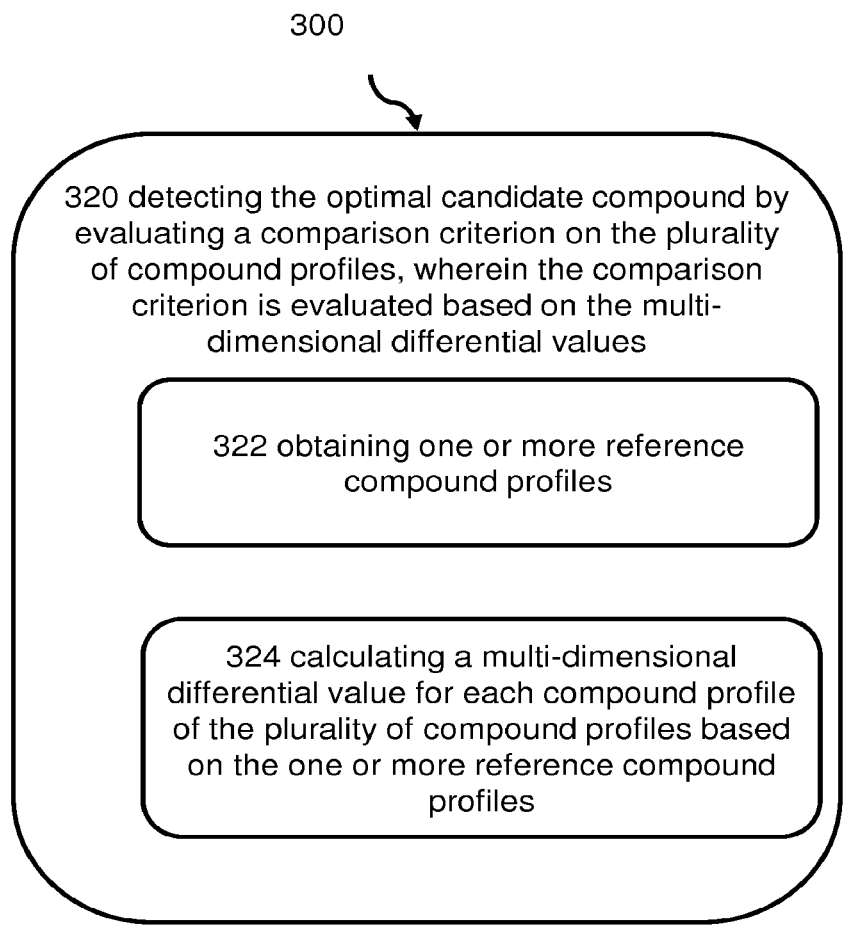
FIG. 5 shows details of a flowchart of a method according to yet an embodiment of the invention.

FIG. 5 shows details of a flowchart of a method according to yet an embodiment of the invention. In an embodiment, the method step of detecting 320 the optimal candidate compound further comprises obtaining 322 one or more reference compound profiles, calculating 324 a multi-dimensional differential value for each compound profile of the plurality of compound profiles based on the one or more reference compound profiles, detecting 320 the optimal candidate compound by evaluating a comparison criterion on the plurality of compound profiles, wherein the comparison criterion is evaluated based on the multi-dimensional differential values.

In an embodiment, the image data is depicting each sample comprised in the concentration gradient 660 from a plurality of field of views 650 and/or the image data is depicting each sample comprised in the concentration gradient 660 processed with a plurality of image filters.

In an embodiment, generating phenotypic profiles further comprises generating a cytometric parameter set for each cell based on the image data to form a first collection of cytometric parameter sets. In an embodiment, generating phenotypic profiles further comprises generating a phenotypic classification model, configured to map a cytometric parameter set to a class, based on a parameter similarity function and the first collection, wherein the parameter similarity function is configured to correlate cytometric parameter sets of the first collection to each other.

In an example, the similarity function is a correlation function, more preferably a multi-dimensional correlation function configured to operate over two or more cytometric parameter sets. In a further example, the similarity function is selected from machine learning techniques, e.g. Self-Organizing Maps, Auto-Encoders, Ward Clustering, K-Means Clustering, t-SNE Dimensionality Reduction.

In an embodiment, generating phenotypic profiles further comprises displaying a deviation measure and/or exclusion criterion based on the cytometric parameter set for each cell, receiving user input data and excluding image data depicting cells based on user input data indicating that the image data is not viable or deviates substantially from the remaining image data set. In one example, the deviation measure and/or exclusion criterion is standard deviation or a distance measure to mean of a cytometric parameter comprised in a cytometric parameter set. An advantage of this embodiment is that it allows the user to evaluate the viability and/or deviation of input and/or intermediate data.

In an example, image data and/or fluorescent images are converted and/or generated into cellular objects associated with cytometric measures and/or cytometric parameter sets. A user then manually searches through the data to build a baseline understanding of an experiment and responses present due to variable changes such as cell lines, chemical compounds, and different concentration. In addition, there are cases where certain image data comprising fields of views are out of focus or have artifacts present in the image data, which affects image processing feature extraction and/or the generation of a cytometric parameter set for each cell. Before generating class-labels and classes for cells, it is important to eliminate aspects of the experiment that are not viable and/or deviates substantially from the remaining data set. With these considerations in mind, the inventors developed a set of analytics, based on a selection of Principal Component Analysis, feature selection using variance thresholds, correlation statistics, e.g. Pearson & Spearman, control reference normalization, object feature vector profiles, hierarchical clustering, and t-distributed stochastic neighbor embedding (t-SNE).

Figure 6:
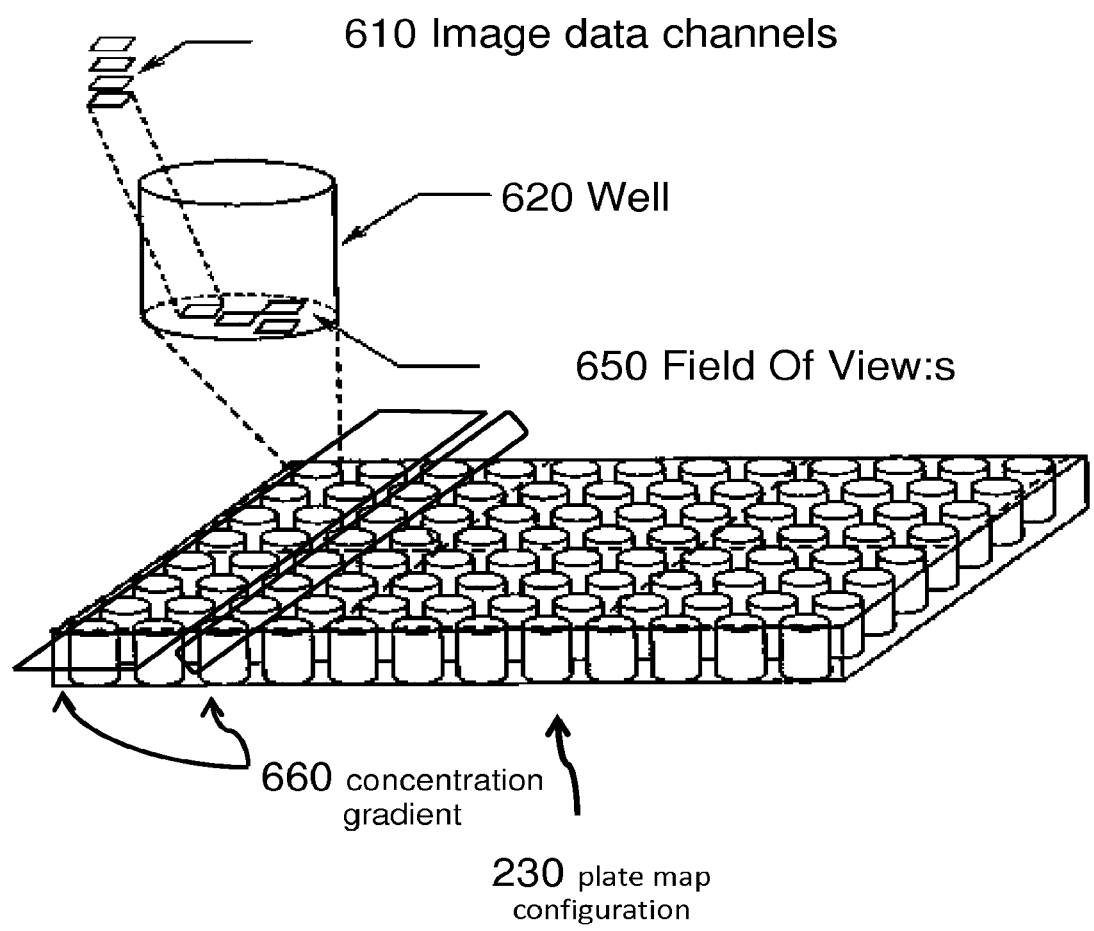
FIG. 6 schematically shows how image data may be generated by an image generator according an embodiment of the invention.

FIG. 6 schematically shows how image data may be generated by an image generator 220. In an embodiment, a plurality of wells 620 is comprised in a plate map configuration 230 and/or a well-plate. A set of the plurality of wells 620 may each comprise samples of a cell line exposed to one or more biomarkers, which may be the same one or more biomarkers, and different concentrations of a candidate compound forming at least one concentration gradient 660. The image generator 220 may be configured to generate and/or capture image data depicting each of the one or more concentration gradients 660, e.g. depicting individually each sample of cells of the samples comprised in each well comprising different concentrations of the candidate compound forming at least one concentration gradient 660. In an example, the image data depicting a well 620 may comprise multiple representations and/or images capturing and/or depicting the sample of cells from a plurality a plurality of field of views 650. In yet an example, the image data depicting a well 620 may comprise one or more source representations and/or source images depicting the sample of cells and a plurality of processed representations and/or processed images generated by processing by a plurality of image filters, such as low-pass, high-pass, averaging or color image filters or any other image filter available to the skilled person. In yet an example, the image data depicting a well 620 may comprise multiple representations and/or images capturing and/or depicting the sample of cells in different image data channels 610 representing different wavelengths of sound, such as ultrasound, or electromagnetic radiation, such as radio, microwave, infrared, visible light, ultraviolet, X-rays and gamma rays.

Figure 7:
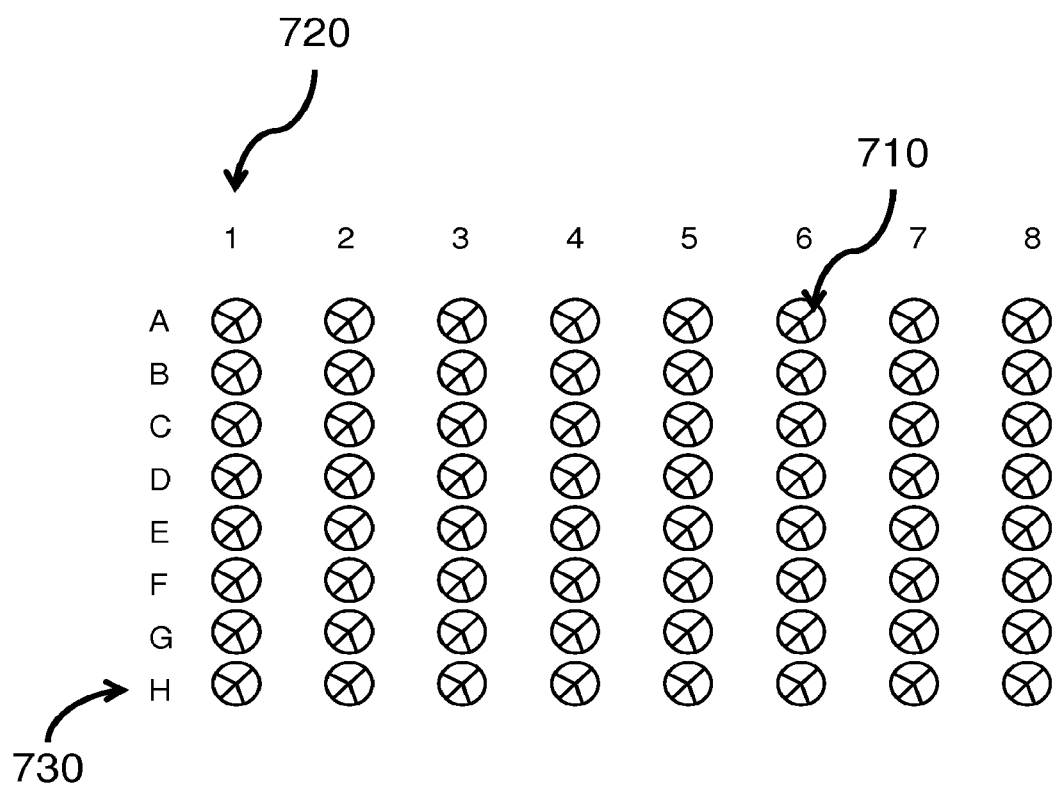
FIG. 7 shows an example of how phenotypic profiles are displayed according to an embodiment of the invention.

FIG. 7 shows an example of how phenotypic profiles are displayed according to an embodiment of the invention, e.g. as a pie chart trellis. In an embodiment, phenotypic profiles are displayed overlaid on a layout of the plate map configuration 230 and/or well-plate. In an embodiment a phenotypic profile 710 of each sample of each well of the plate map configurations 230 and/or well-plate is displayed. In an example, the pie chart trellis of Compound 1 with having a Concentration A is shown as a pie chart indicating, 8 cells classified as "dead", 12 cells classified as "not dead" and 6 cells classified as "other". In a further embodiment, the phenotypic profiles 710 are arranged in columns 720 and rows 730. In a further embodiment, a concentration gradient is arranged along wells in a column 720 of the plate map configuration 230 and/or well-plate.

In an example, the phenotypic profiles is displayed as a visualizations dashboard as a pie chart trellis across the layout of the plate. An advantage is that a user would quickly understand how a population varied across samples arranged on the plate map. To increase the granularity, well-to-well comparisons could prove as a good source of analysis. Because wells across a column tend to vary in different concentrations and/or drug dosage and wells across a row tend to vary in the candidate compound and/or type of drug. These comparisons are absolutely critical in post-classification analysis. The inventors realized that a biologist would want to know if a class of cells survived under a particular drug or what percentage of them survived under a particular dosage. In a further example, the user may view the phenotypic profiles and provide user input data indicating that the image data is not viable and/or deviates substantially from the remaining data set, thus providing the user with the ability to filter out features that are not of value. In yet an example, if a user were analyzing a certain population, and wanted to see how that population varied with respect to area, they could filter out all the features sans area to investigate that particular trend.

Figure 8:
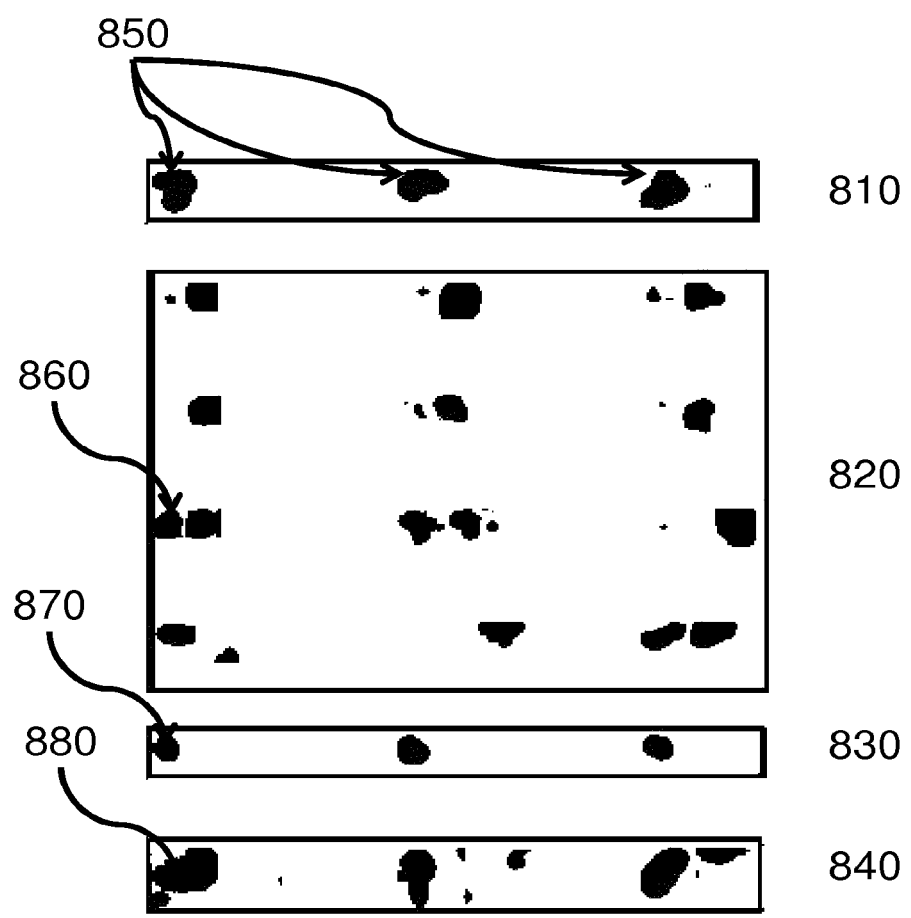
FIG. 8 shows an example of displaying an exemplary subset of image data and a respective class according to an embodiment of the invention.

FIG. 8 shows an example of displaying an exemplary subset of image data and a respective class according to an embodiment of the invention. In an example, an exemplary subset of image data depicting at least one cell of the samples for each class have been selected and is displayed together with respective class-label and/or class 810-840 to a user. In particular, the exemplary subset of image data depicting three cells 850 of a sample for a first class 810 have been selected and is displayed together with respective class-label and/or class 810 to a user. The user may then indicate an operation on at least one class 810-840 and the computer device 100, according to the disclosure, will perform the operation on the class-label and/or class of cells of the cell lines based on the user input data. The operation may be selected from "add class", "delete class", "split class" or "merge class". In yet an example including cell cycle perturbation, a single well-characterized cell line had been treated with and/or exposed to different concentrations of two different candidate compounds, which perturb the cell cycle progression by interfering with cell division or inducing cell death. This study requires both the classification of the cells into known sub-populations by cell cycle status and also defining cell health status based on the presence of a fluorescent biomarker for dead cells, e.g. indicating a health status of "dead", "not dead", or "other". The result of applying the method of the present disclosure would result in a first exemplary subset of image data 850 being displayed together with respective first class-label and/or class 810 "not dead". Further an exemplary second subset of image data 860 is displayed together with a respective second class-label and/or class 820 "dead". Further an exemplary third subset of image data 870 is displayed together with a respective third class-label and/or class 830 "not dead". Further an exemplary fourth subset of image data 880 is displayed together with a respective fourth class-label and/or class 840 "other". After the user realizes that the first and third class "not dead" should be classified as the same class, the user may choose to join/merge those two, thereby updating all cells in the first and third class-label and/or class to indicate the first class-label and/or class.

In one usecase, two biomarkers in the form of fluorescent proteins and/or fluorophores can be used to stain cells—DAPI to stain nucleus or nucleic acid or Nuclei and Cy5 can be used to stain dead cells. Based on these stains, one possible clustering result, when using the present invention to generate a class-label and a class for each cell of the samples and/or using unsupervised clustering, is as follows:

Cluster/Class 1: DAPI: Nuclear brightness, roundish, Cy5: no brightness indicating live cells;
  Cluster/Class 2-3: DAPI: Dim brightness, irregular shapes of nuclei, Cy5: very bright indicating dead cells; Cluster 4-5: DAPI: Medium brightness, round oval shape, Cy5: bright indicating dead cells;
  Cluster/Class 6: DAPI: very bright, uniform brightness of small nucleus, Cy5: no brightness indicating live cells;

Cluster/Class 7: DAPI: uneven spread of brightness, non-uniform labeling, Cy5: Light labeling, noisy.

Exemplary subsets for each of these clusters are presented to a user who may choose to keep Clusters 1, 6, 7 as is and combine Clusters 2, 3, 4, and 5. Although this decision is made based on exemplary subset of image data, regrouping is applied based on the decision to the entire dataset.

Figure 9:
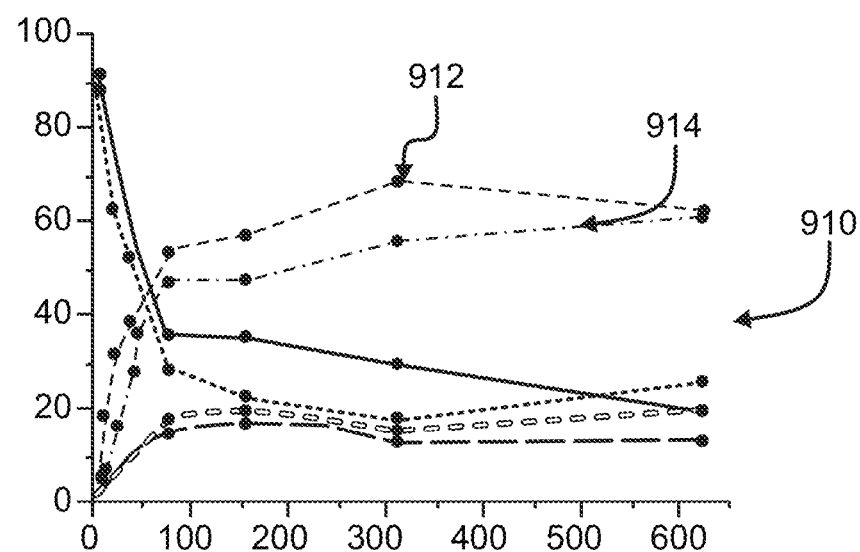
FIG. 9 shows an example of a comparison between phenotypic profiles generated by the method according to the invention and generated by a manual method.
Figure 9:
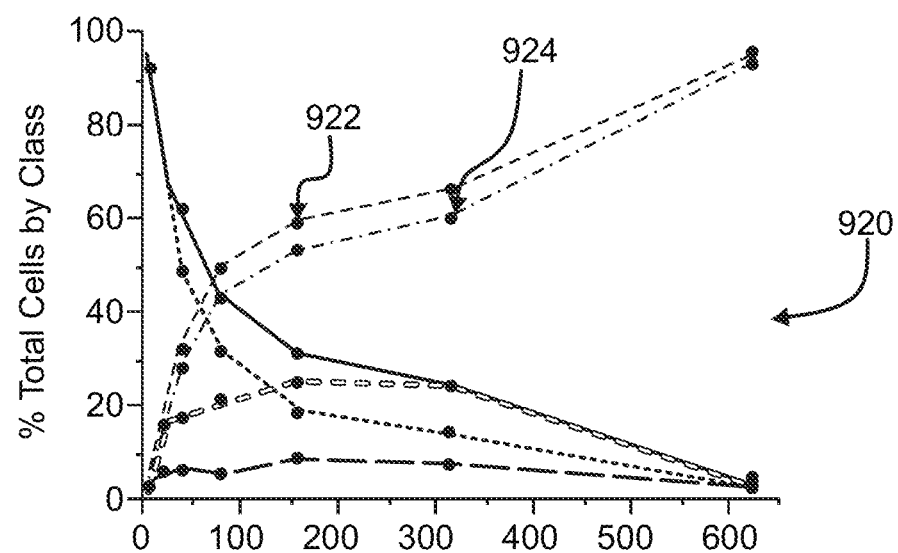

FIG. 9 shows an example of a comparison between phenotypic profiles generated by the method according to the invention and generated by a manual method. A phenotypic profile may comprise data points for a cell count of cells classified to belong to a particular class for each sample exposed to each concentration of a concentration gradient. A phenotypic profile may comprise data points for multiple classes and/or multiple concentration gradients. In the top diagram 910 the number of cells classified to a first class by the method of the present invention is shown in a first curve 914 and the number of cells classified by the manual method to the first class is shown in a second curve 912. In the bottom diagram 920 the number of cells classified to a second class by the method of the present invention is shown in a first curve 924 and the number of cells classified by the manual method to the second class is shown in a second curve 922. The curves indicate cell count of cells classified to a class versus concentration of the candidate compound. In the example, the method of the present invention differed from the manual method by 7% but achieved classification 24 times faster. In an example with reference to FIG. 7, an experiment with eight candidate compounds [Compound 1, Compound 2, . . . , Compound 8] each with a concentration gradient [Concentration A, Concentration B, . . . , Concentration H] is processed by the method and computer device of the present disclosure. At a first point in time $T_0$ of a plurality of successive points in time a phenotypic profiles is generated for each concentration gradient of each candidate compound, e.g. as:

Compound 1, Concentration A, 8 (class dead), 12 (class not dead)

Compound 1, Concentration B, 4 (class dead), 16 (class not dead)

...

Compound 1, Concentration H, 2 (class dead), 18 (class not dead)

Figure 10:
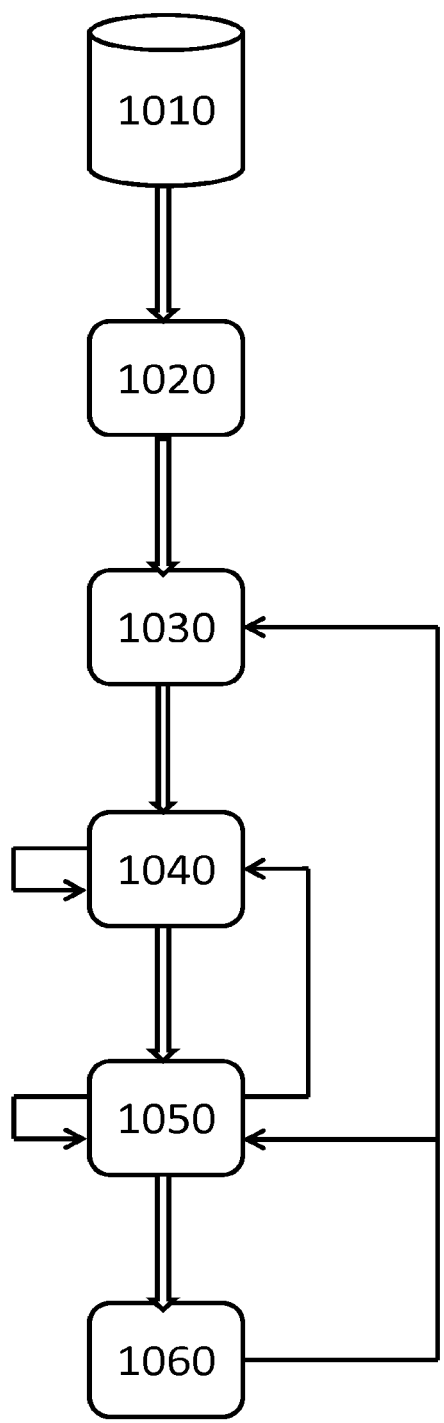
FIG. 10 shows a flowchart of a method for a computer device, for detecting an optimal candidate compound based on a plurality of samples according to an embodiment of the invention.

FIG. 10 shows a flowchart of a method for a computer device 100, for detecting an optimal candidate compound based on a plurality of samples according to an embodiment of the invention. In an embodiment, the method comprises object sampling 1010 and/or segmenting cell objects from image data. In an embodiment, the method further comprises generating a respective corresponding cytometric parameter for each cell object. The method may further comprise running an unsupervised clustering algorithm 1030 to generate intrinsic groupings 1040 and/or generating a class-label and/or a class and/or a group for each cell object based on the image data. The method may further comprise exemplar sampling and/or selecting an exemplary subset of image data depicting at least one cell object and/or one cell of the samples for each class-label and/or class. The method may further comprise model grouping and/or receiving user input data from a user indicative of an operation on at least one class and performing the operation on the class-label and/or class of cells of the samples based on the user input data, where the operation on at least one class is selected from add class, delete class, split class or merge class. Optionally, the method may further comprise generating a phenotypic classification model, e.g. an expression-based model expression-based model.

Furthermore, any methods according to embodiments of the invention may be implemented in a computer program, having code means, which when run by processing means causes the processing means to execute the steps of the method. The computer program is included in a computer readable medium and/or memory of a computer program product. The computer readable medium may comprise of essentially any memory, such as a ROM (Read-Only Memory), a PROM (Programmable Read-Only Memory), an EPROM (Erasable PROM), a Flash memory, an EEPROM (Electrically Erasable PROM), or a hard disk drive.

Moreover, it is realized by the skilled person that the computer device 100 comprise the necessary communication capabilities in the form of e.g., functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processors of the present computer device 100 may comprise, e.g., one or more instances of a Central Processing Unit (CPU), a processing unit, a processing circuit, a processor, an Application Specific Integrated Circuit (ASIC), a field-programmable gate array (FPGA), a microprocessor, or other processing logic that may interpret and execute instructions. The expression "processor" may thus represent a processing circuitry comprising a plurality of processing circuits, such as, e.g., any, some or all of the ones mentioned above. The processing circuitry may further perform data processing functions for inputting, outputting, and processing of data comprising data buffering and device control functions, such as call processing control, user interface control, or the like.

Finally, it should be understood that the invention is not limited to the embodiments described above, but also relates to and incorporates all embodiments within the scope of the appended independent claims.

The invention claimed is:

1. A computer-implemented method for generating class-labels and/or classes for cells comprising:
   obtaining image data associated with a plurality of samples of a cell line treated with a biomarker and subjected to experimental perturbation;
   segmenting, by a processor, cell objects from the obtained image data;
   generating a set of class-labels corresponding to each of the cell objects;
   running an unsupervised clustering algorithm on the processor to classify each of the cell objects with a corresponding one of the set of class-labels;
   displaying at least one cell object and the respective class-label;
   receiving data indicative of an operation on at least one class-label; and
   performing the operation on the class-label by the processor based on the received data.

2. The method of claim 1, wherein experimental perturbation comprises at least one of: inhibiting enzyme activities in cells, promoting enzyme activities in cells, genetic modification of cells, or applying a candidate compound to cells.

3. The method of claim 2 wherein applying a candidate compound comprises applying different concentrations of the candidate compound to the cells forming a concentration gradient.

4. The method of claim 1, wherein the operation comprises one of add class, delete class, split class, and merge class.

5. The method of claim 1, wherein displaying at least one cell object and the respective class-label comprises displaying an exemplary cell object and the respective class-label and/or class comprises:
    calculating a confidence measure of how well each cell object represents the class-label; and
    selecting the exemplary cell object as the cell object with the highest confidence measure.

6. The method of claim 1 wherein the class-label is indicative of cell health status or cell cycle status.

7. The method of claim 1, further comprising generating phenotypic profiles of a concentration gradient for a candidate compound at each of a plurality of successive points in time to form a compound profile.

8. The method of claim 7, further comprising forming a first collection of cytometric parameter sets by generating a cytometric parameter set for each cell object based on the image data.

9. The method of claim 1, further comprising storing at a memory a phenotypic classification model based upon the class-labels, wherein the phenotypic classification model is configured to map a cytometric parameter set to a class, based on a parameter similarity function.

10. The method of claim 9, wherein the parameter similarity function is a multi-dimensional correlation function configured to operate over two or more cytometric parameter sets.

11. The method of claim 10, wherein the parameter similarity function is a machine learning algorithm selected from the group consisting of: self-organizing maps, auto-encoders, Ward Clustering, K-Means Clustering, and t-SNE Dimensionality Reduction.

12. The method of claim 1, further comprising:
    detecting an optimal candidate compound selected from one or more reference compound profiles and based on the experimental perturbation; and
    calculating a multi-dimensional differential value for each of the one or more reference compound profiles based on the experimental perturbation.

13. A system comprising:
    a computer-readable medium storing instructions that, when executed by a processor:
        obtain, by the processor, image data associated with a plurality of samples of a cell line treated with a biomarker and subjected to experimental perturbation;
        segment cell objects from the obtained image data;
        generate a set of class-labels corresponding to each of the cell objects; and
        run an unsupervised clustering algorithm on the processor to classify each of the cell objects with a corresponding one of the set of class-labels;
        render for display at least one cell object and respective class-label from the obtained image data, wherein the rendered displayed at least one cell objects are segmented based upon the classification from the unsupervised clustering algorithm;
        receive data indicative of an operation on at least one class-label; and
        perform the operation on the class-label by the processor based on the received data.

14. The system of claim 13, wherein the operation comprises one of add class, delete class, split class, and merge class.

15. The system of claim 13, wherein displaying at least one cell object and the respective class-label comprises displaying an exemplary cell object and the respective class-label and/or class comprises:
    calculating a confidence measure of how well each cell object represents the class-label; and
    selecting the exemplary cell object as the cell object with the highest confidence measure.

16. The system of claim 13, wherein the class-label is indicative of cell health status or cell cycle status.

17. The system of claim 13, wherein the processor further generates phenotypic profiles of a concentration gradient for a candidate compound at each of a plurality of successive points in time to form a compound profile.

18. The system of claim 17, wherein the processor further forms a first collection of cytometric parameter sets by generating a cytometric parameter set for each cell object based on the image data.

19. The system of claim 13, further comprising storing at the computer-readable medium a phenotypic classification model based upon the class-labels, wherein the phenotypic classification model is configured to map a cytometric parameter set to a class, based on a parameter similarity function.

20. The system of claim 13, wherein the processor is further configured to:
    detect an optimal candidate compound selected from one or more reference compound profiles and based on the experimental perturbation; and
    calculate a multi-dimensional differential value for each of the one or more reference compound profiles based on the experimental perturbation.

* * * * *